United States Patent
Holberg

(10) Patent No.: US 7,383,163 B2
(45) Date of Patent: Jun. 3, 2008

(54) METHOD, DEVICE AND COMPUTER PRODUCT FOR MAKING AN INDIVIDUAL MODEL OF A JAW-BONE

(76) Inventor: Christof Holberg, Jochbergweg 1, 82393 Iffeldorf (DE)

( * ) Notice: Subject to any disclaimer, the term of this patent is extended or adjusted under 35 U.S.C. 154(b) by 166 days.

(21) Appl. No.: 10/502,555

(22) PCT Filed: Jan. 22, 2003

(86) PCT No.: PCT/EP03/00610

§ 371 (c)(1),
(2), (4) Date: Feb. 9, 2005

(87) PCT Pub. No.: WO03/063085

PCT Pub. Date: Jul. 31, 2003

(65) Prior Publication Data

US 2005/0143967 A1    Jun. 30, 2005

(30) Foreign Application Priority Data

Jan. 23, 2002    (DE) ............................... 102 02 515

(51) Int. Cl.
  G06G 7/48      (2006.01)
  G06G 7/64      (2006.01)
  G09B 23/28     (2006.01)
  G09B 23/00     (2006.01)
  G09B 23/30     (2006.01)
  A61B 5/05      (2006.01)
  A61B 5/055     (2006.01)

(52) U.S. Cl. ............................... 703/6; 703/10; 703/11; 434/263; 434/264; 434/267; 434/274; 600/416; 600/425

(58) Field of Classification Search ................... 703/6, 703/10, 11; 434/263, 264, 267, 274; 600/416, 600/425
See application file for complete search history.

(56) References Cited

U.S. PATENT DOCUMENTS 4,611,247 A * 9/1986 Ishida et al. ............... 358/3.01

(Continued)

FOREIGN PATENT DOCUMENTS

EP    0 741 994 A1    11/1996

OTHER PUBLICATIONS

Kober et al., "Linear Elastic Modelling of the Human Mandible", Oct. 29, 2001, http://www.zib.de/Numerik/numsoft/kardos/projects/mandible.html, 5 pgs.*

(Continued)

Primary Examiner—Kamini S Shah
Assistant Examiner—Suzanne Lo
(74) Attorney, Agent, or Firm—David W. Carstens; Carstens & Cahoon, LLP

(57) ABSTRACT

The invention relates to a method, a device and a computer software for making an individual model of a jawbone, which are particularly useful in the development of dental implants or pre-operative planning of implants. The method comprises the following steps: making a tomogram of a jawbone perpendicular to the longitudinal axis of the jawbone; determining the boundary of the jawbone and the surrounding tissue and the boundary between the compact and spongiosal portion of the jawbone; transforming said boundaries into a two-dimensional profile; and extruding the two-dimensional profile into a three-dimensional volume body model of the jawbone. The volume body model of the jawbone may be combined with the volume body model of an implant and then transformed into a finite element model.

21 Claims, 15 Drawing Sheets

U.S. PATENT DOCUMENTS

Figure 1:

| | | | | |
|---|---|---|---|---|
| 5,452,407 | A | * | 9/1995 | Crook ........................ 345/421 |
| 5,921,927 | A | * | 7/1999 | McArdle .................... 600/425 |
| 6,408,044 | B2 | * | 6/2002 | Sembritzki et al. ........... 378/15 |
| 6,442,288 | B1 | * | 8/2002 | Haerer et al. ................ 382/128 |
| 6,687,529 | B2 | * | 2/2004 | Van Vaals ................... 600/417 |
| 6,932,842 | B1 | * | 8/2005 | Litschko et al. ......... 623/16.11 |
| 2001/0021806 | A1 | * | 9/2001 | Gueziec et al. ............. 600/425 |
| 2002/0082779 | A1 | * | 6/2002 | Ascenzi ....................... 702/19 |
| 2003/0065259 | A1 | * | 4/2003 | Gateno et al. .............. 600/425 |
| 2003/0068075 | A1 | * | 4/2003 | Faber et al. ................ 382/131 |
| 2003/0169913 | A1 | * | 9/2003 | Kopelman et al. .......... 382/132 |
| 2005/0037320 | A1 | * | 2/2005 | Poirier ....................... 433/173 |

OTHER PUBLICATIONS

Geopak, "Geopak 2001MR" Chapter 20, 2001, 11 pages.*

L. Mutlu-Sagesen et al., A Three-Dimensional Model Of The Mandible Using Two-Dimensional CT Images, 2001 Proceedings of the 23rd Annual EMBS International Conference, Oct. 25-28, Istanbul, Turkey, pp. 2778-2781.

D. Perie et al., Tomodensitometry Measurements For In Vivo Quantification Of Mechanical Properties Of Scoliotic Vertebrae, Clinical Biomechanics 16 (2001) pp. 373-379.

Paul P. Van Zyl, BChD, et al., Three-Dimensional Finite Element Model Of A Human Mandible Incorporating Six Osseointegrated Implants For Stress Analysis Of Mandibular Cantilever Prostheses, The International Journal of Oral & Maxillofacial Implants, pp. 51-57.

J. W. Farah et al., Finite Element Analysis Of A Mandibular Model, Journal of Oral Rehabilitation, 1998, vol. 15, pp. 615-624.

Von Priv.-Doz. Dr. rer. nat. Heinz Handels, Medizinische universitat zu Lubeck, Medizinische Bildverarbeitung, B.G. Teubner Stuttgart—Leipzig 2000.

Benutzerhandbuch, AutoCAD 2000, Apr. 1999.

* cited by examiner

METHOD, DEVICE AND COMPUTER PRODUCT FOR MAKING AN INDIVIDUAL MODEL OF A JAW-BONE

The present invention relates to a method, a device and a computer software for making an individual model of a jawbone, which is particularly useful in the development of dental implants or pre-operative planning of implants.

The success of an implant insertion depends decisively on the distribution of chewing forces and stresses that are introduced via the implant into the jawbone. Besides shape and size of the implant the individual shape and composition of the jawbone is an important factor.

From the prior art, various finite element models (FE models) of jawbones are known, but these models do not stand the test in practice unconditionally.

For example, Farah J, Craig R and Meroueh K: "Finite element analysis of a mandibular model", Journal of Oral Rehabilitation 16, 603-11 (1989) suggests directly constructing a two-dimensional model of a lower jaw in an FE program (see attached FIG. 14). This method makes the attempt to copy the complex configuration of the jawbone as good as possible in a two-dimensional way, but it does not result in a morphological exact transfer of the configuration into the three-dimensional space. Due to the simplification of the complex geometry, this method is at best useful for solving basic problems. Individual morphological features, however, are left unconsidered. What is more, the manual construction of the model is time-consuming, tiresome and error-prone.

On the other hand, van Zyl P, Grundling N, Jooste C and Terblanche E: "Three-dimensional finite element model of a human mandible incorporating six osseointegrated implants for stress analysis of mandibular cantilever prostheses", International Journal of Oral Maxillofac Implants 10, 51-7 (1995) describes a three-dimensional FE model of a lower jawbone which is not constructed but which is generated from tomograms of a real lower jaw (see attached FIG. 15). In this method, a point cloud obtained from the tomograms is directly input into a FE program where the points of the point cloud are used as nodes for the FE model. The current FE programs, however, have difficulties with making a three-dimensional network from dense point clouds, so that this approach works only in certain cases while mostly losses in the representation of the complex morphological configuration have to be accepted. As a rule, the FE program must therefore be adapted to the specific application under a high expenditure of time, a measure which can only be carried out by experts and results in isolated applications.

The object of the invention is to provide a method, a device and a computer software capable of generating an individual model of the jawbone, with relatively low expenditure of time and good accuracy.

The above object is solved, for example, by a method in which a tomogram of the jawbone is made in a direction perpendicular to the longitudinal axis of the jawbone and which comprises the following image processing steps: i) determining the boundary of the jawbone and the surrounding tissue based on the tomogram; ii) transforming the boundary between the jawbone and the surrounding tissue into a two-dimensional profile; and iii) extruding the two-dimensional profile to obtain a three-dimensional solid model (also known as a "volume body model") of the jawbone.

The technical term "extruding" means that the two-dimensional profile is extended in a certain direction (i.e. in the direction of the longitudinal axis of the jawbone) to give volume to the model. In other words, the profile is drawn along a path until a predetermined end position is reached. The extrusion path may run along the surface normal given by the two-dimensional profile, but it may also deviate from the normal and be adjusted closer to the exact run of the longitudinal axis of the jawbone.

The method according to the invention takes advantage of the fact that the jawbone does hardly change its inherently complex configuration in the longitudinal direction over a short distance such as across a gash.

For developing dental implants, usually a model of the jawbone having a length corresponding to a gash (having a width of about 5-10 mm) is sufficient. Therefore, it is fully adequate if only a single tomogram of the jawbone is made to obtain the two-dimensional profile, which is then extruded in the direction of the longitudinal axis of the jawbone across the width of the gash to obtain the three-dimensional solid model. Thus, the proposed method gets by with relatively few image data. That is why the image processing step i) to iii) can be executed fast and time-saving. Nevertheless, the method is sufficiently exact for the individual features of the jawbone be taken into account.

If the accuracy of the solid model is to be increased or if the configuration of the jawbone is to be reproduced over a longer distance, it is also possible to make a plurality of tomograms in the direction of the longitudinal axis of the jawbone and to generate the three-dimensional solid model by extruding across the respective profiles obtained thereby. In this case, the solid model spans the respective profiles and has a cross section that changes in accordance with the profile outline.

If the composition of the jawbone is of particular importance for respective fields of application of the model, the boundary between the spongiosal and compact portion of the jawbone may be determined in addition to the boundary of the jawbone and the surrounding tissue to generate a two-part solid model of the spongiosal and compact jawbone.

The solid model of the jawbone may be transformed into the three-dimensional finite element model (FE model) either directly or after combining it with the solid model of a dental implant and/or tooth. Combining the solid model with the dental implant and/or tooth is a further image processing step iv). The geometry of a solid model can be made into a high-resolution FE network with relative ease, so that not much time is required for generating the FE model.

If different material properties are assigned to the respective parts of the FE model (i.e. the jawbone and the dental implant or tooth), complex calculations can be made by means of the FE model, for example, relating to the distribution of stress in the jawbone when a force acts on the dental implant and/or the tooth.

The above method may be carried out, for example, by using a device which comprises an equipment for making a tomogram of a jawbone in a direction perpendicular to the longitudinal axis of the jawbone, and a data processor for executing the following data processing steps: reading and, if need be, digitizing one or a plurality of tomograms of the jawbone made by the equipment; and executing the above-mentioned image processing steps i) to iii) and optionally iv) by means of CAD techniques (CAD: computer aided design) to generate a three-dimensional solid model of a jawbone or a jawbone combined with a dental implant and/or tooth. Concerning the image processing step iii) in which the two-dimensional profile is extruded to obtain the three-dimensional solid model, in particular the CAD techniques "extruding", "sweeping" and "lofting" come into question.

The solid models generated by means of the CAD techniques may be transformed by CAD-FEM-coupling into individual FE models.

It goes without saying that the invention may be realized, instead of using the above device, by a computer software which implements the above-mentioned data processing steps based on software routines when running on a computer. The computer software may be stored on a data carrier or may be directly loaded into the working memory of the computer.

The data processing steps may be automated to the greatest possible extent, so that the invention is made available even to a non-professional who has no experience in the field of CAD or FE programs. Moreover, automation avoids inaccuracies and errors inevitable in case a model is directly constructed. Owing to the fact that the invention may use software routines known from current CAD and FE programs, it is possible to avoid isolated applications.

Figure 2:
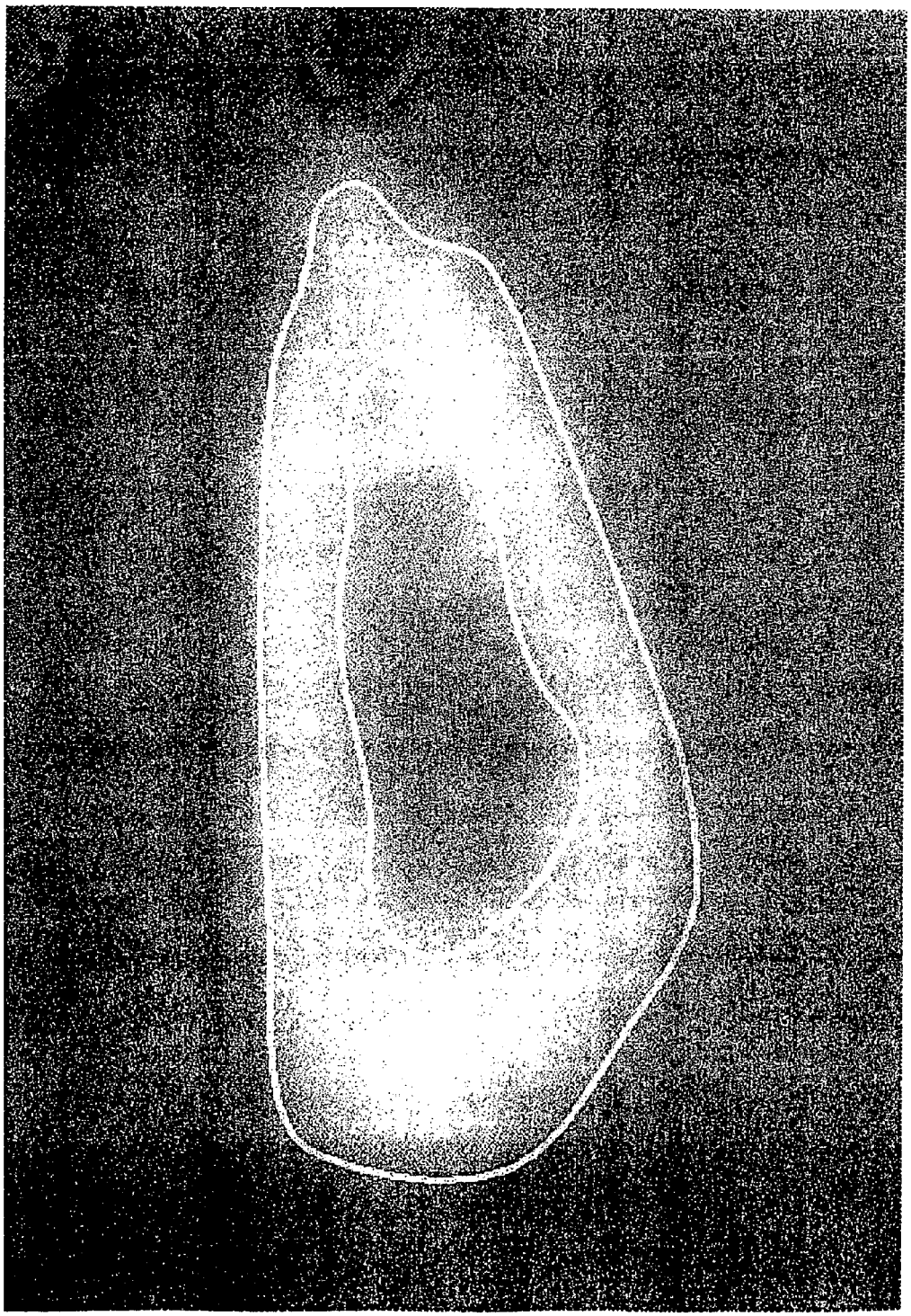
Figure 3:
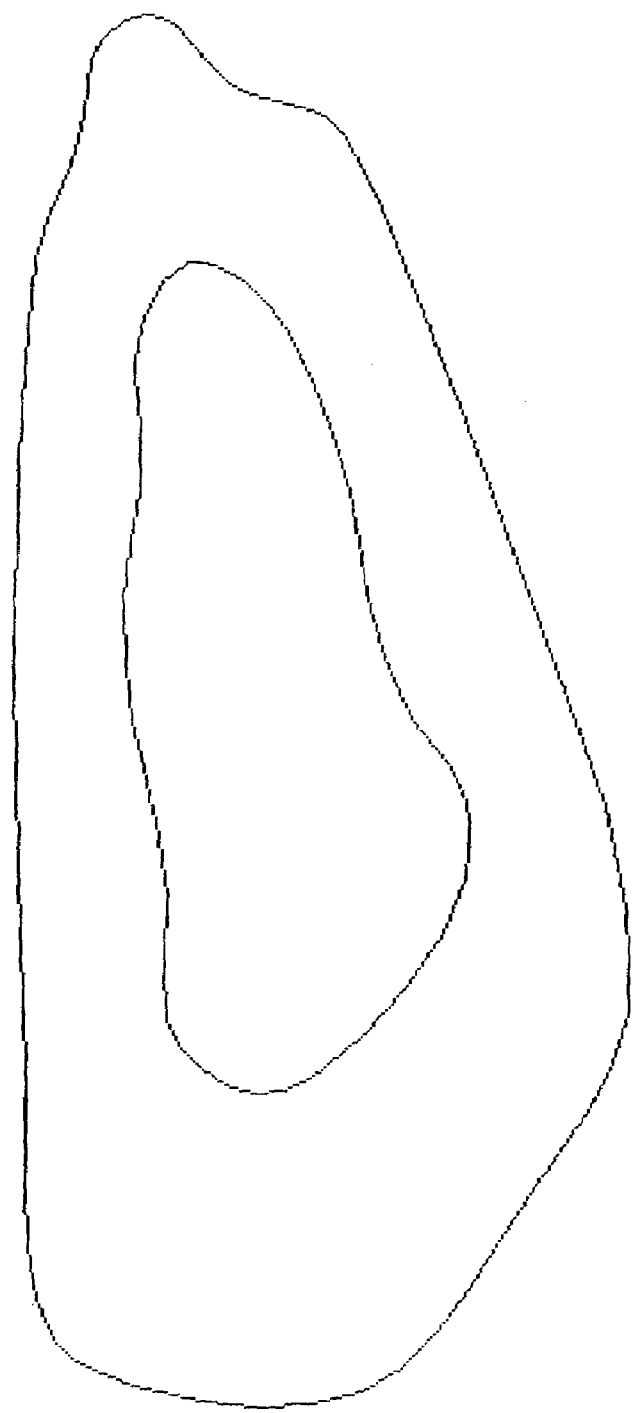
Figure 4:
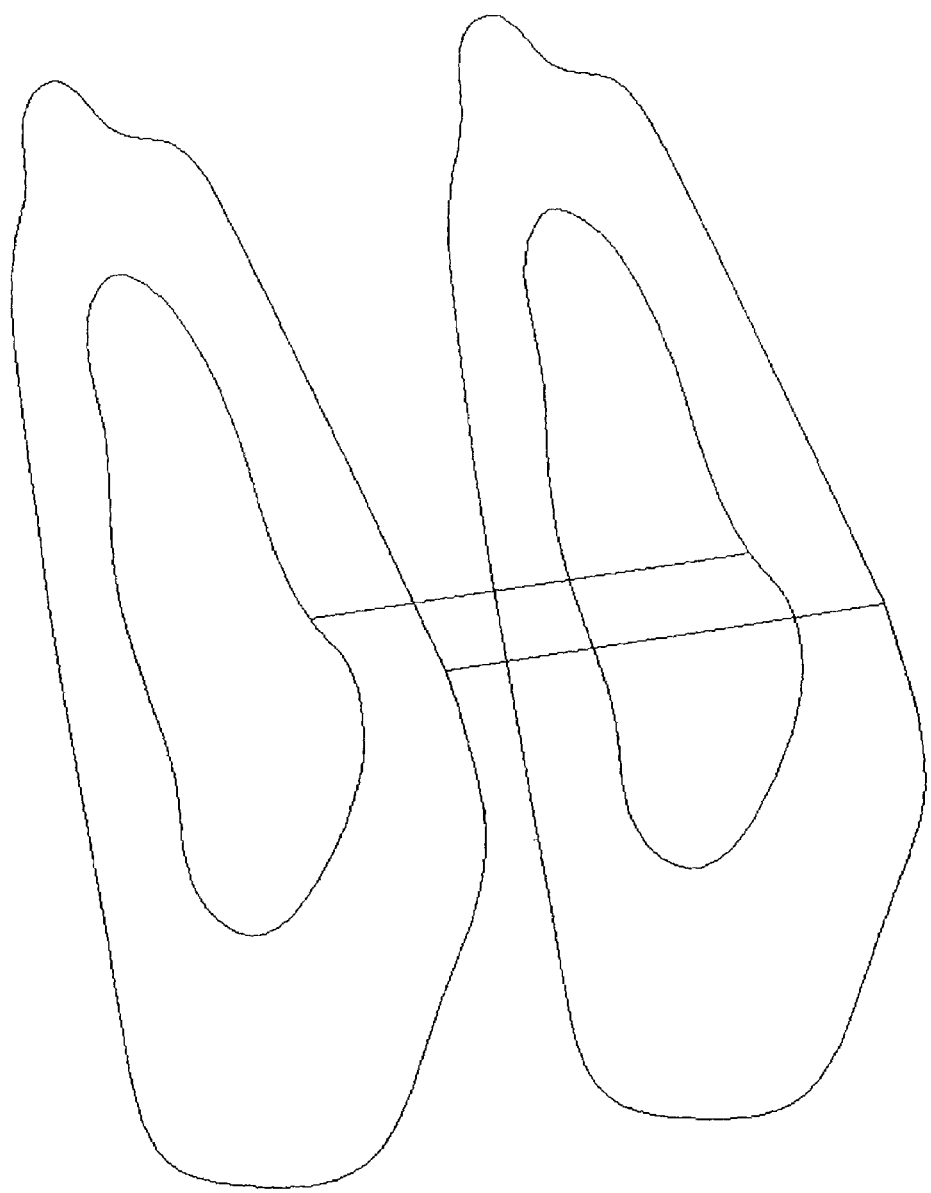
Figure 5:
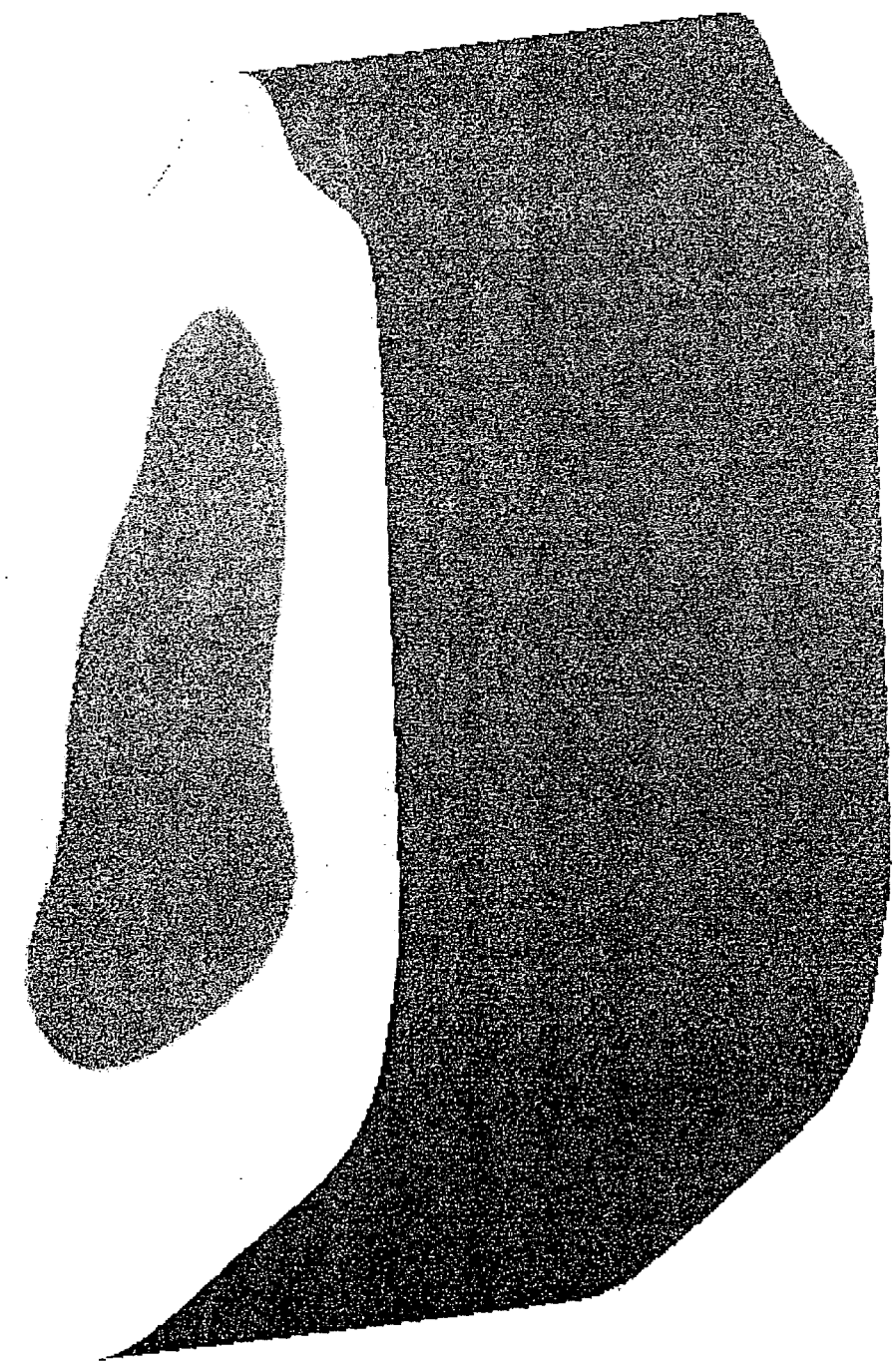
Figure 6:
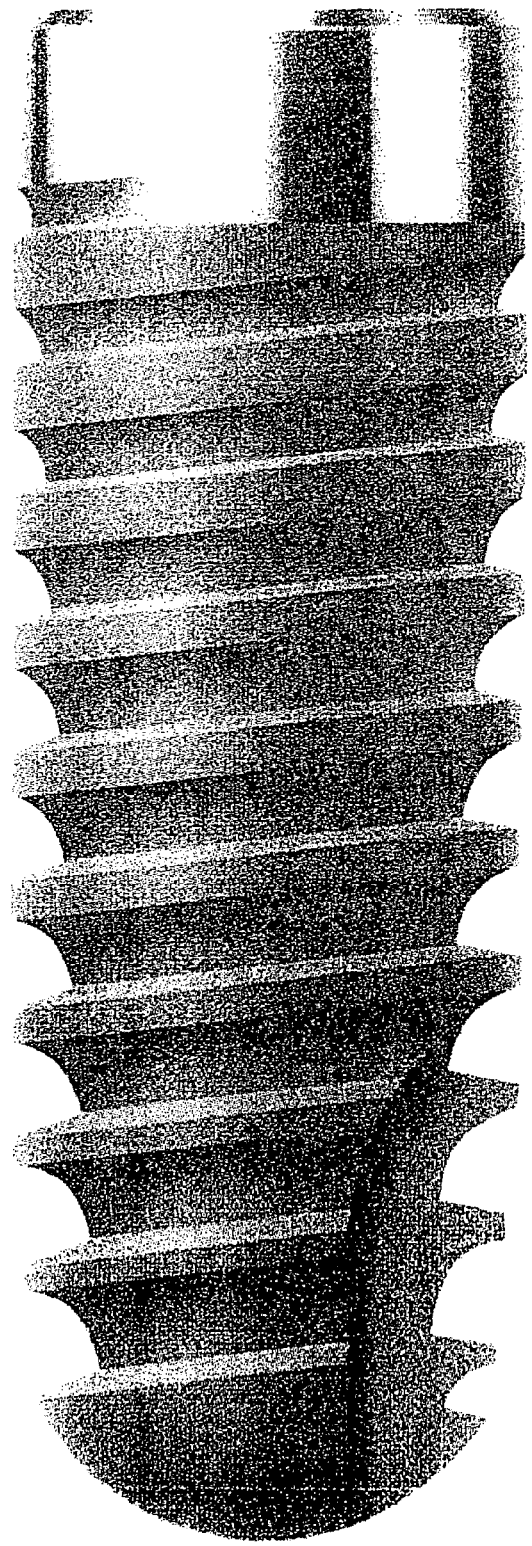
Figure 7:
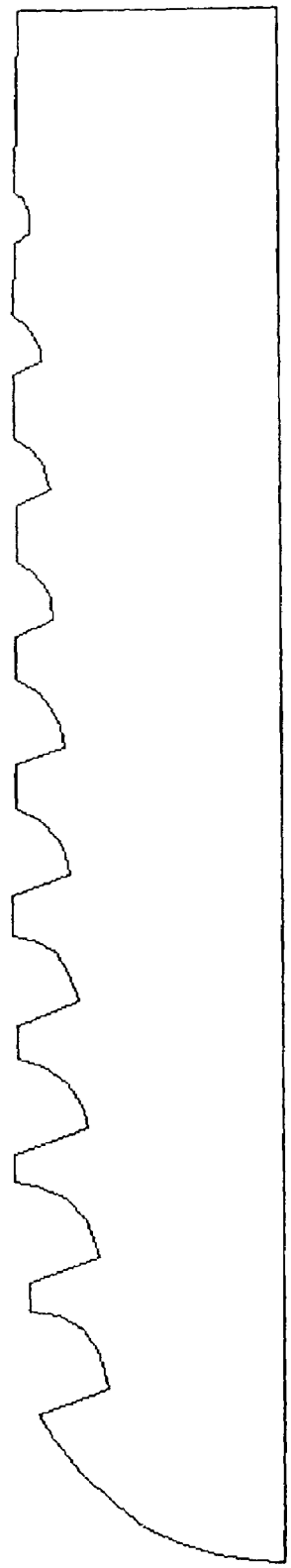
Figure 8:
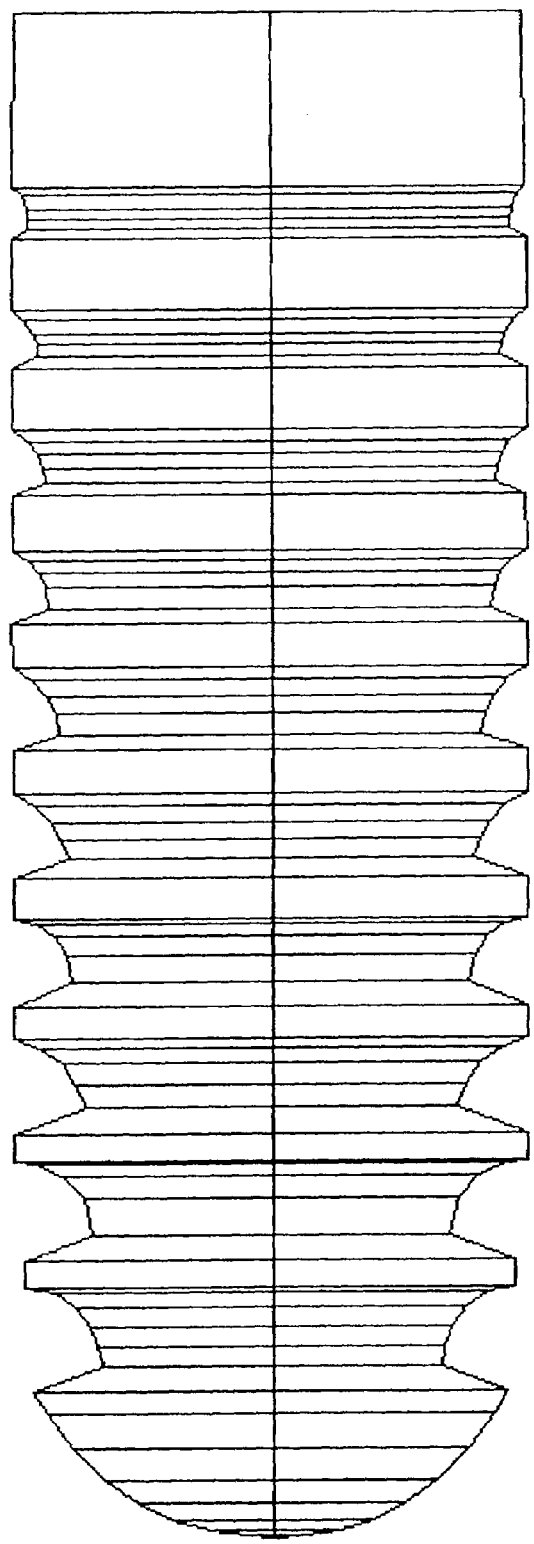
Figure 9:
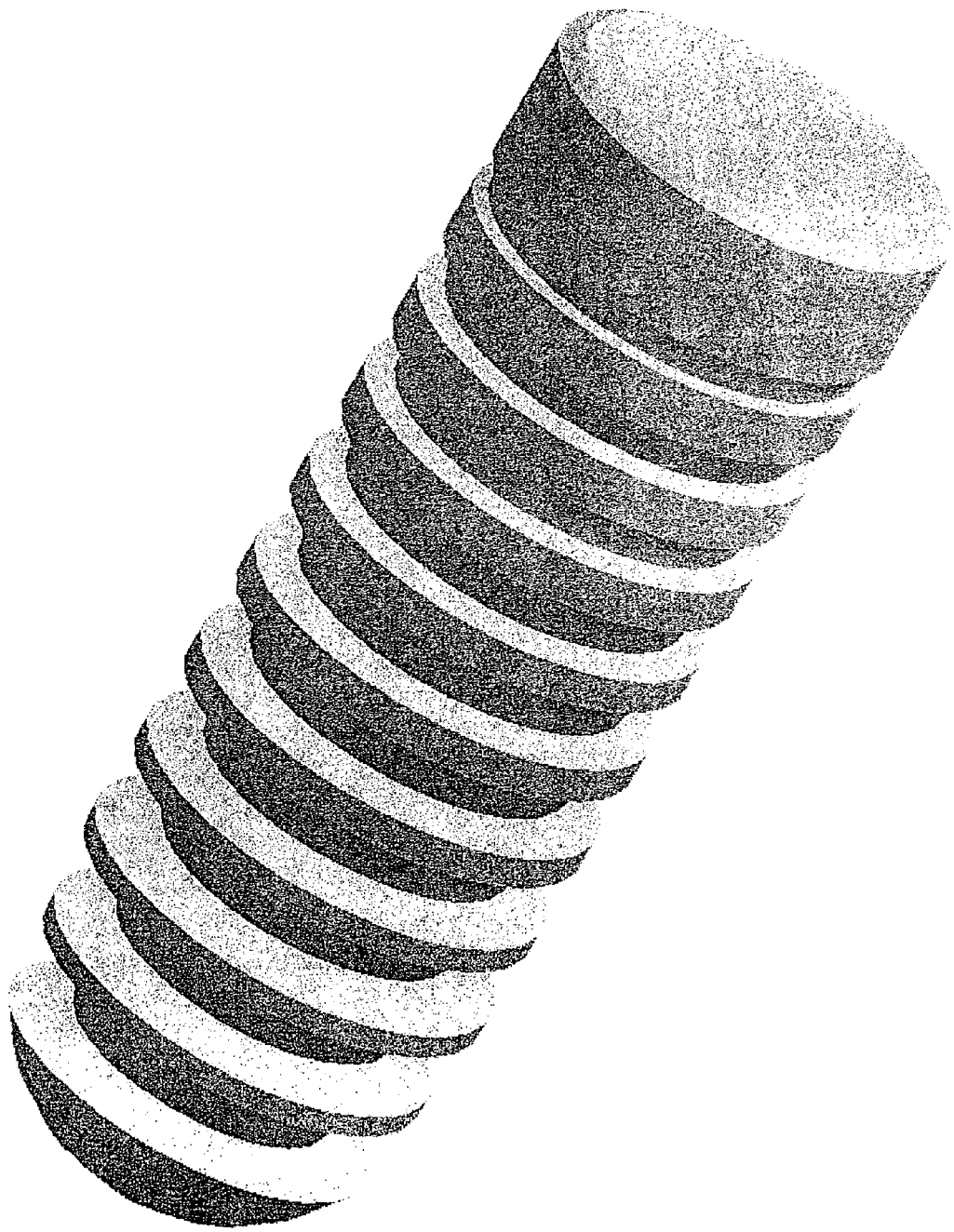
Figure 10:
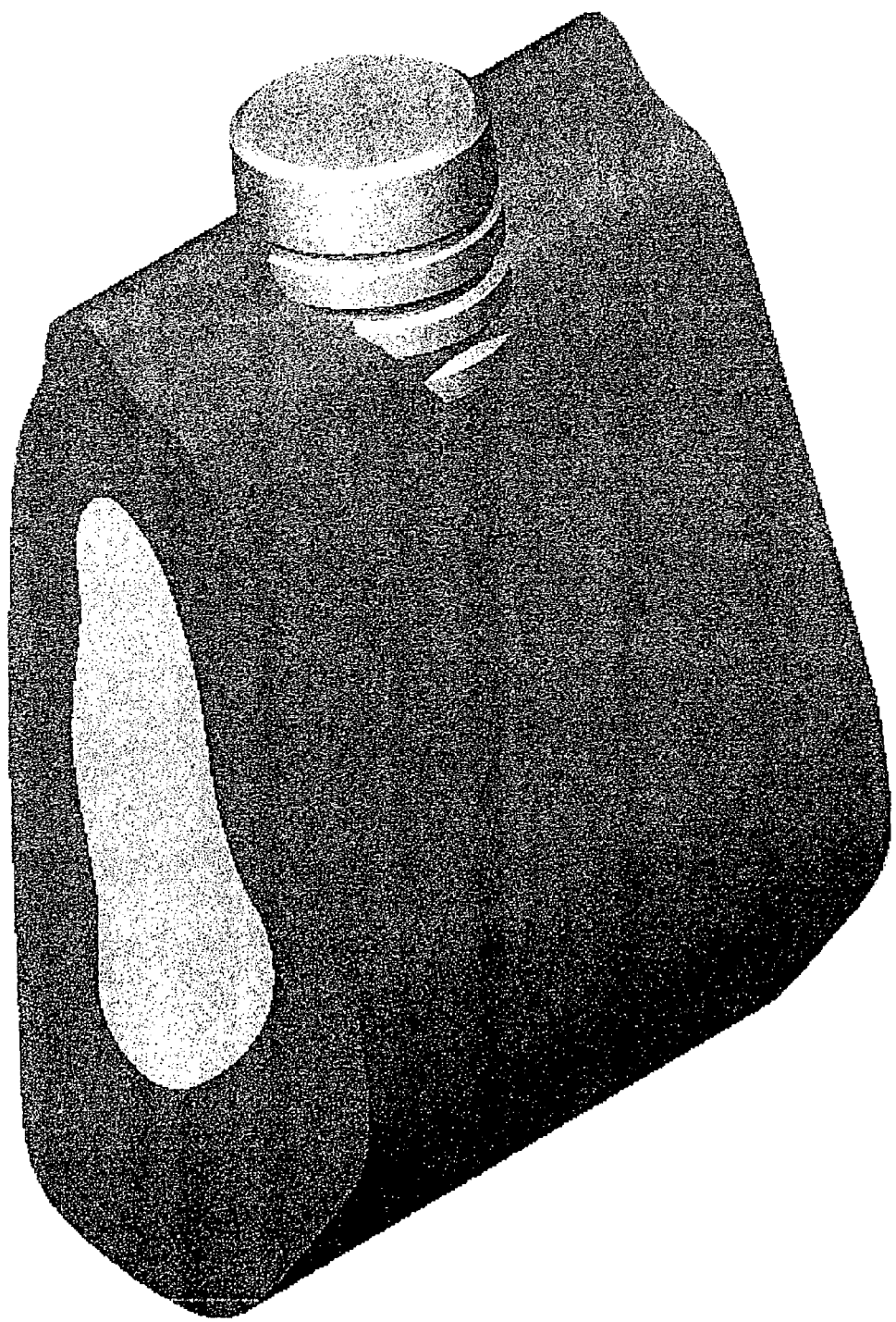
Figure 11:
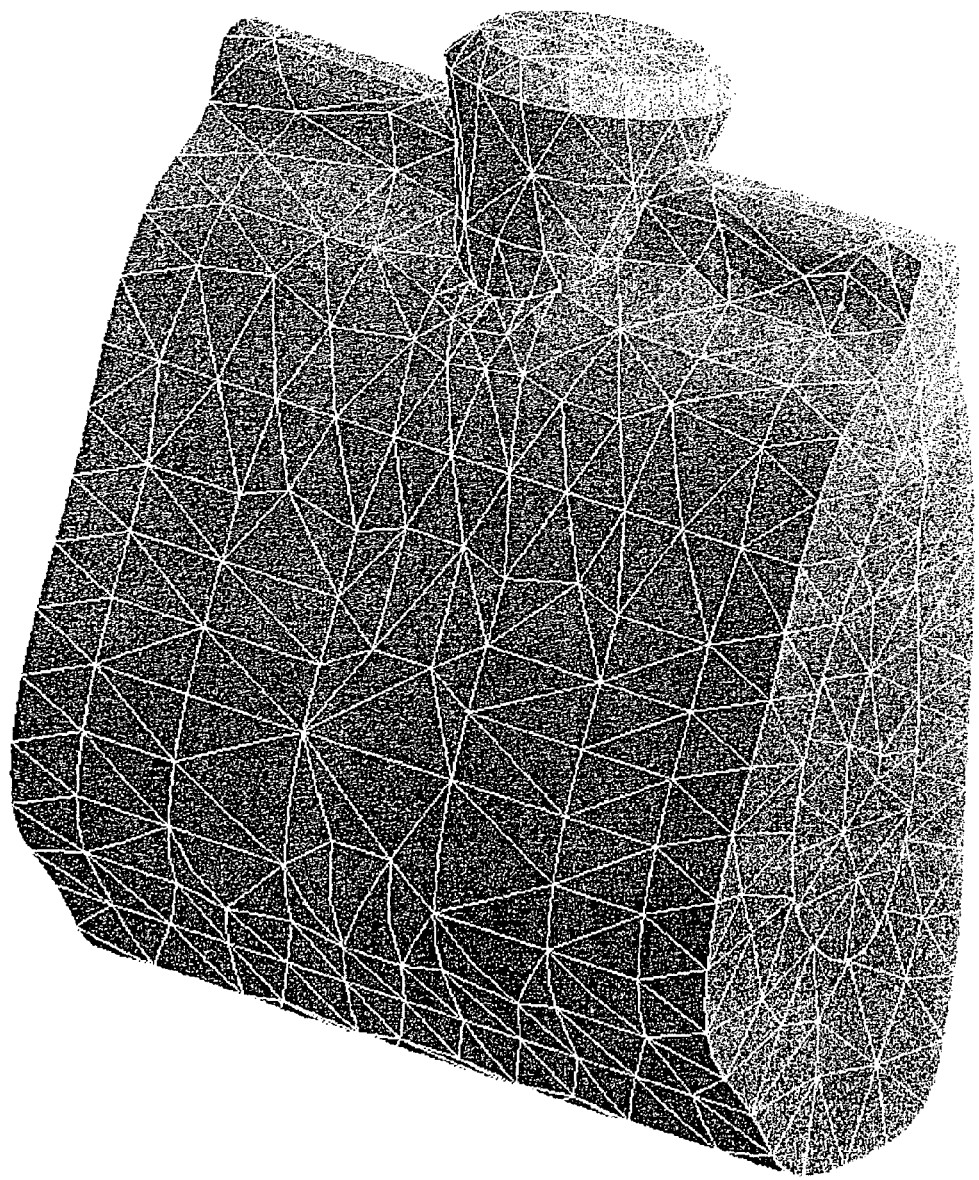
Figure 12:
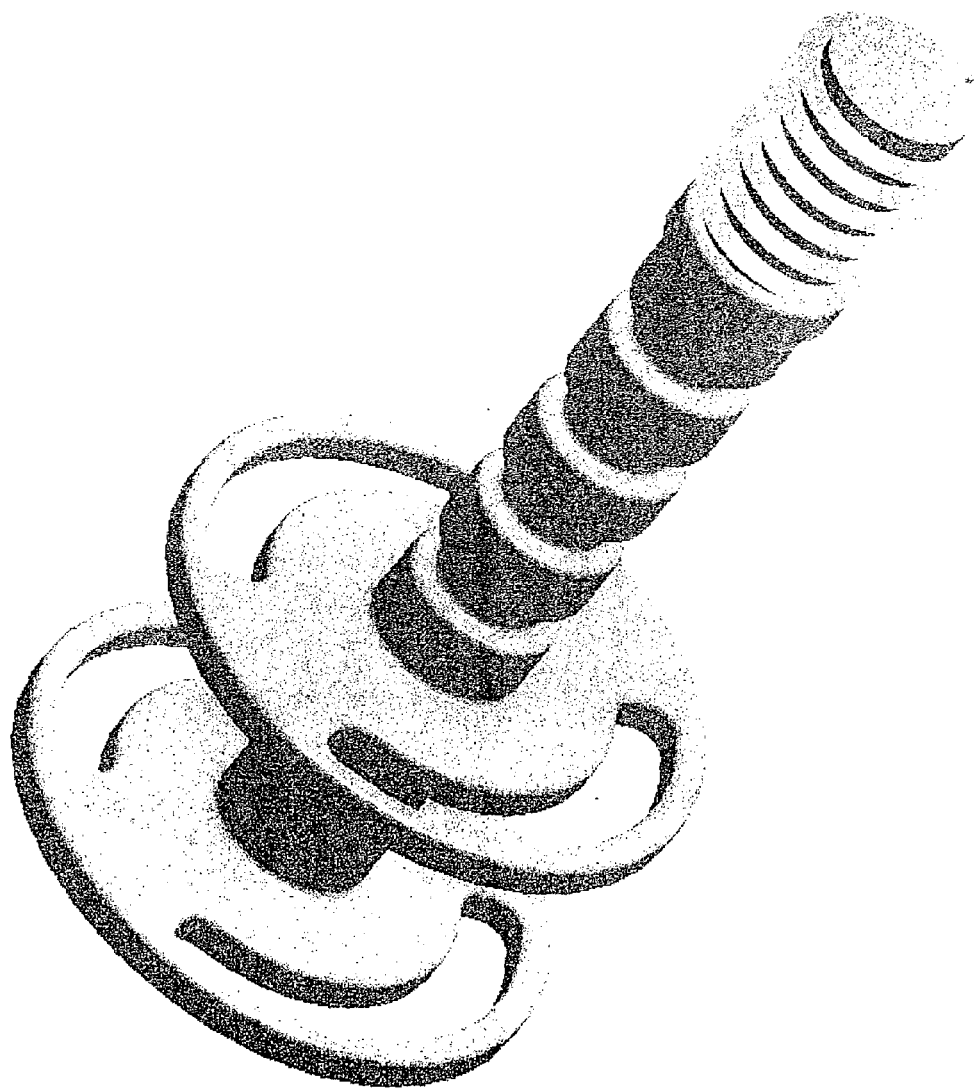
Figure 13:
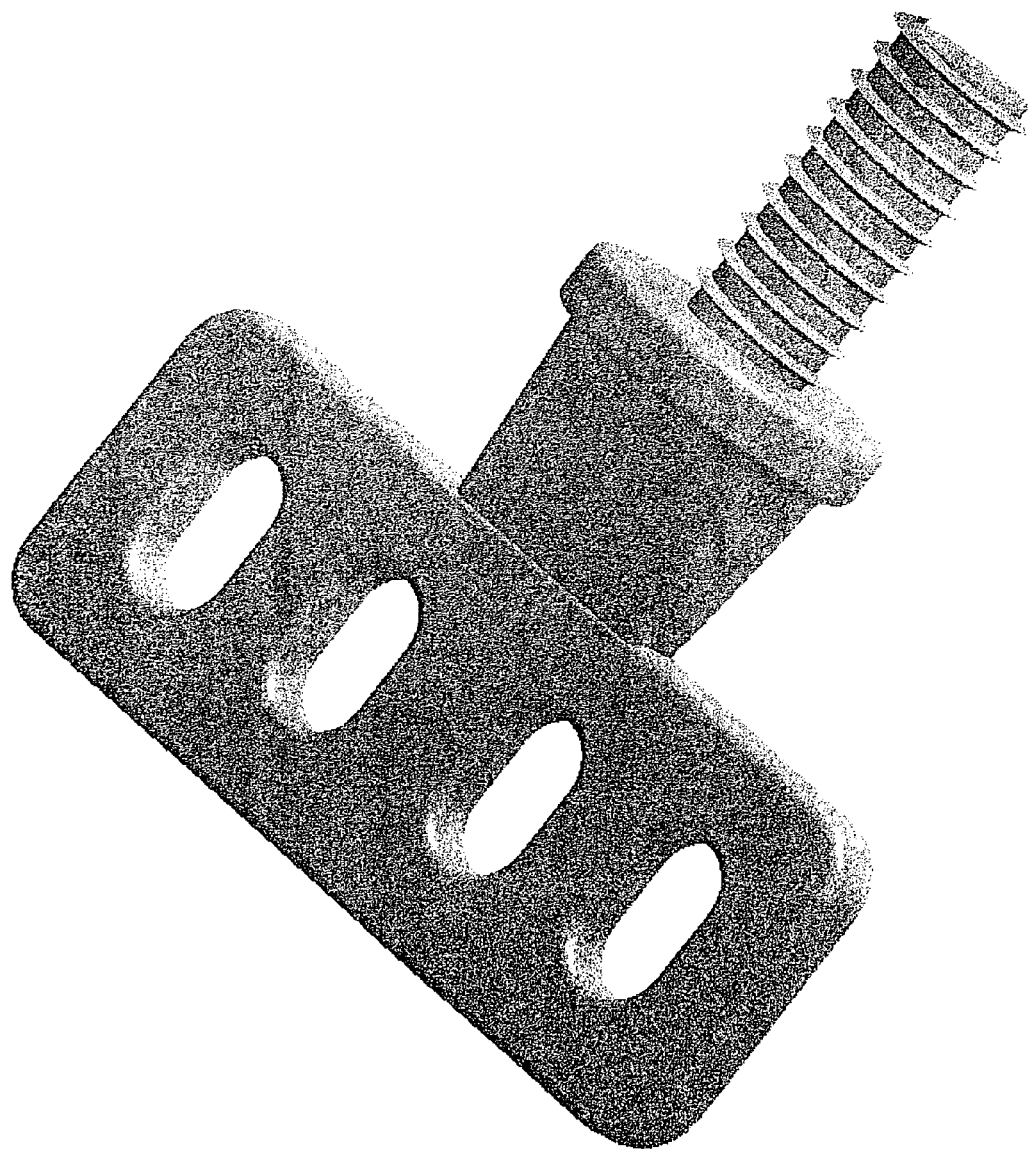
Figure 14:
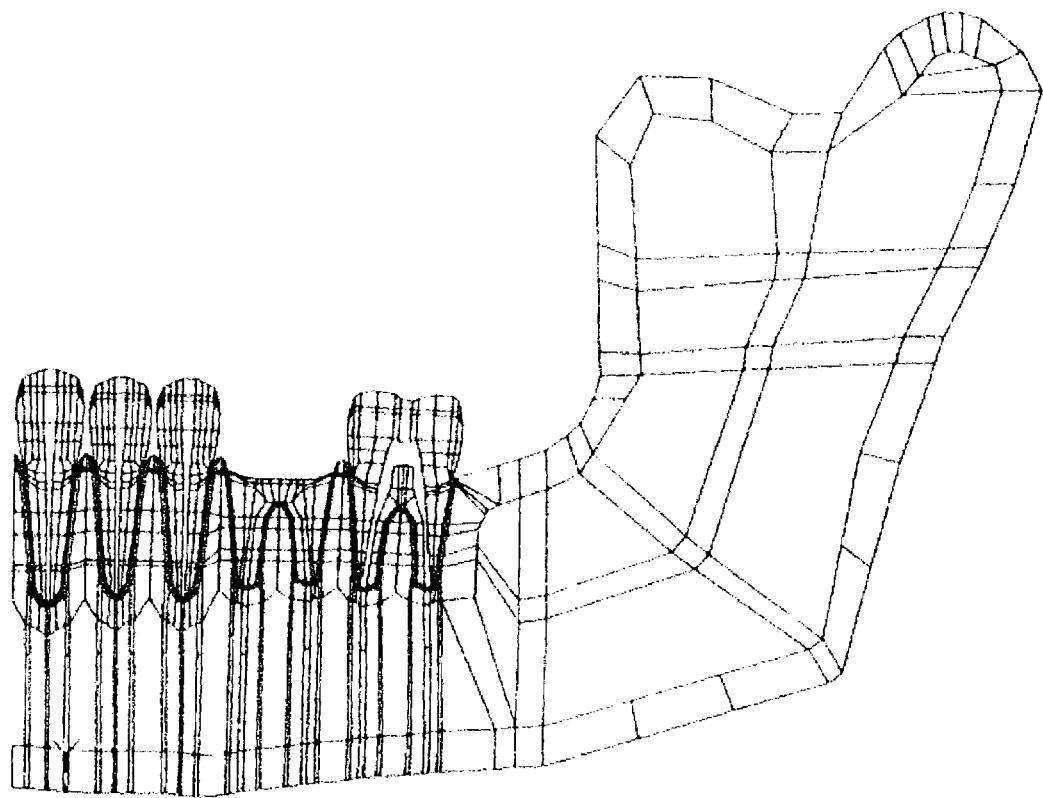
Figure 15:
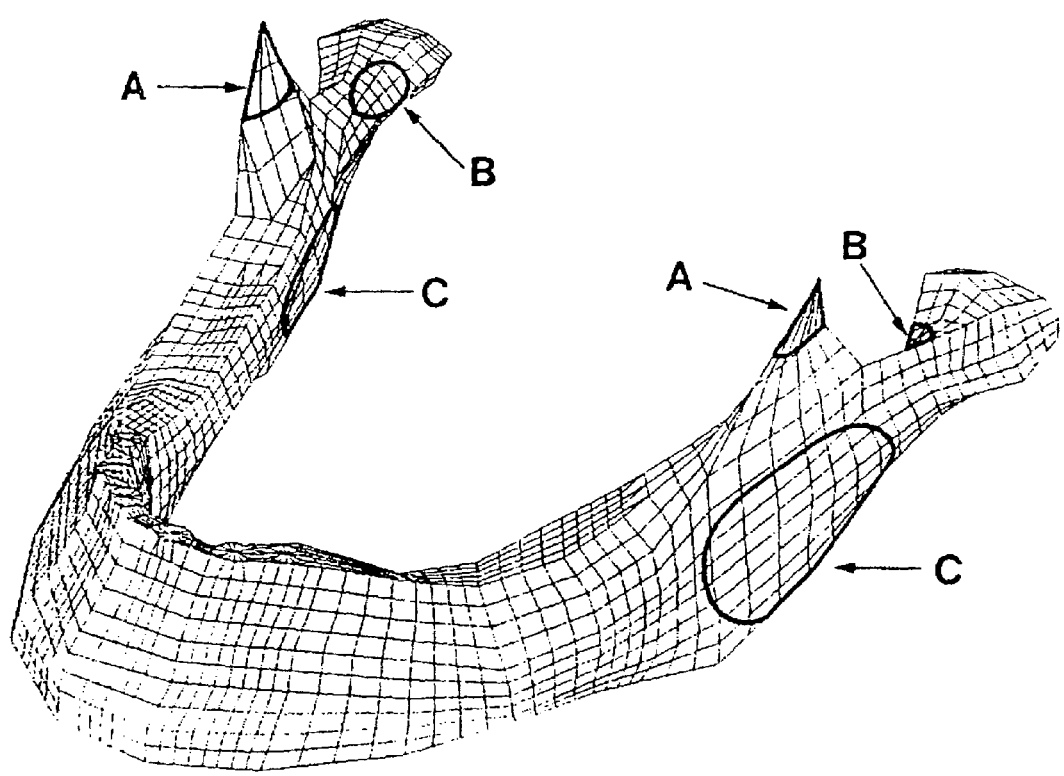

The above and further solutions to the object of the invention as well as the features and advantages thereof are now discussed in more detail by referring to specific embodiments of the invention. The description of the embodiments is to be read with the accompanying drawings which show the following:

FIG. 1 an X-ray tomogram in a direction perpendicular to the longitudinal axis of an upper and lower jaw;

FIG. 2 a magnified section of the X-ray tomogram of FIG. 1 in which the boundary of the spongiosal and compact lower jawbone is marked;

FIG. 3 a two-part profile of the spongiosal and compact bone, which has been generated from FIG. 2;

FIG. 4 a wire frame image of a three-dimensional solid obtained by extruding the profile of FIG. 3;

FIG. 5 a surface image of the solid model of FIG. 4;

FIG. 6 a photography of a cylinder-type implant;

FIG. 7 a half profile of the implant shown in FIG. 6;

FIG. 8 a wire frame image of a three-dimensional solid model obtained by rotating the half profile shown in FIG. 7 around the center line by 360°;

FIG. 9 a surface image of the solid model of FIG. 8;

FIG. 10 a surface image of a three-part solid model obtained by combining the solid models shown in FIGS. 5 and 9;

FIG. 11 a three-dimensional FE model of a spongiosal and compact lower jawbone with an implant;

FIG. 12 a surface image of a three-dimensional solid model of a disc-type implant;

FIG. 13 a surface image of a three-dimensional solid model of a sheet-type implant;

FIG. 14 a two-dimensional FE model of a lower jaw half according to the state of the art; and FIG. 15 a three-dimensional FE model of a lower jaw according to the state of the art.

In the following, an application is described in which an individual model of a patient's lower jaw is generated and the lower jaw model thus generated is combined with a model of a cylinder-type implant. The steps for generating the lower jaw model and the implant model and the way of combining both models are discussed separately.

Generating the Lower Jaw Model

Using an equipment for making a tomogram in the vicinity of a gash where insertion of an implant is planned, a tomogram is made in a direction perpendicular to the longitudinal axis of the lower jawbone. FIG. 1 shows such a tomogram transversal to the longitudinal axis of the lower jaw, which has been made by using a digital volume tomography apparatus (DVT).

Since the obtained tomogram is already digital, it can be imported without previous scanning into a CAD program (e.g. Mechanical Desktop™ of Autodesk Inc.), which runs on a data processor such as a work station. The tomogram is scaled such that the dimensions in the CAD program correspond to the dimensions of the tomogram.

In the CAD program a two-dimensional sketch of the spongiosal and compact lower jawbone is prepared, with the tomogram serving as a drawing pattern in the background. As shown in FIG. 2, at that time the boundaries between the compact portion (light gray) of the bone and the surrounding tissue (dark gray) and between the spongiosal portion (dark gray) and the compact portion (light gray) of the bone are marked with lines, polylines, or splines.

After having served as a drawing pattern, the tomogram may be cleared. The remaining two-dimensional sketch is further processed and converted into a two-dimensional profile as shown in FIG. 3. The tolerance values of the CAD program (for the angle etc.) are preferably set such that a one-to-one conversion is obtained which is geometrically as exact as possible.

Afterwards, the two-dimensional profile is extruded, as shown in FIGS. 4 and 5, along the surface normal given by the profile to be transformed into a three-dimensional solid model. The extrusion length depends on the patient's gash and is in the present case 10 mm.

The solid model of the lower jawbone thus obtained consists of two parts, namely an inner part defining the spongiosal portion of the bone and an outer part defining the compact portion of the bone. The solid model is a good approximation of the individual shape and composition of the jawbone in the vicinity of the gash.

Generating the Implant Model

At first, a photography of the cylinder-type implant to be used for implant insertion is taken. FIG. 6 shows a longitudinal view of the implant.

The photography is scanned into the above-mentioned CAD program and is scaled to the size of the lower jaw image data. Then, the outline of the implant is marked in the CAD program by lines, polylines or splines, with the photography being in the background. For reasons of simplicity, only half of the outline is taken, resulting in the half profile sketch shown in FIG. 7.

After the photography has been cleared, the half profile sketch of the implant is converted into a profile which is transformed into a three-dimensional solid model by rotating it around the center line by 360°. Contrary to the real implant, this solid model, which is shown in FIGS. 8 and 9, is axially symmetric. Neglecting the lead, however, is irrelevant for the calculations described below.

Combining the Lower Jaw Model with the Implant Model

The solid model of the cylinder-implant shown in FIG. 9 is subtracted from the solid model of the lower jawbone shown in FIG. 5 by applying Boolean-difference operation. Then, the solid model of the cylinder-type implant is inserted into the resulting recess. By doing so, the three-dimensional solid model shown in FIG. 10 is obtained, in which the spongiosal and compact bone is combined with the implant.

Then, the three-part solid model thus obtained is read via a CAD-FEM interface (e.g. by using the instruction AMACISOUT in the program Mechanical Desktop™ of Autodesk Inc.) into an FE program (e.g. Design Space™ of Ansys Inc.). As shown in FIG. 10, the complex geometry of the three-part solid model is transformed by the FE program into a high-resolution three-dimensional FE network.

At the time of generating the FE model, different material properties (e.g. different coefficients of elasticity) are assigned to the spongiosal and compact portion of the lower jawbone and the dental implant. After having determined the bearings and loads, the distribution of stress as well as deformation and strain in the jawbone can be simulated for the case that a force (e.g. a chewing force) is introduced via the implant into the jawbone.

The results obtained from the above FE model can be used for checking the compatibility of the implant with the individual shape and composition of the patient's jawbone. If, for example, a particular large compressive stress develops in certain areas of the jawbone, there is the risk that the bone will be decomposed in these areas after implant insertion, thus impairing the long-term prognosis for the implant. In this case it should be checked whether an implant having a different size or shape offers a better prognosis. FIGS. 11 and 12 exemplify further solid models of a disc-type implant and a sheet-type implant, which have been reproduced from a photography in a similar way as the solid model of the cylinder-type implant shown in FIG. 9 and which may be combined with the solid model of the lower jawbone shown in FIG. 5 to obtain comparative results.

The results obtained from the above FE models may also be used for manufacturing implants that are specifically adapted to the individual jaw anatomy so as to transmit the chewing force to the jaw in an optimal way. The results may also be used for optimizing ready-made implants as well as for manufacturing individual, non-ready-made implants.

MODIFICATIONS

Since the upper jaw does hardly change its complex configuration in the direction of its longitudinal axis across a short distance, the above teaching may also be applied to the upper jaw.

Further, the tomogram of the jawbone may be taken by an equipment other than a digital volume tomography (DVT) apparatus. Examples for such an equipment are, for example, conventional or spiral-type computer tomography (CT) apparatuses, nuclear magnetic resonance (NMR) apparatuses, or sonographic apparatuses. In principle, images of histologic sections can be used as well.

When the tomogram of the jawbone is not digital, the tomogram may be digitized by scanning or the like and be read into the data processor for further processing. However, the bone boundaries may also be determined graphically by counterdrawing or the like, and then digitizing the sketch thus obtained and reading it into the data processor.

Instead of tracing or counterdrawing the bone boundaries manually, the bone boundaries may automatically be detected by the data processor based on the existing difference in brightness value. By doing so, it is possible to improve the reproducibility of the results.

In the above-mentioned application, only a single tomogram was used for generating the jawbone model to minimize the work load and the computational effort. However, it is also possible to take several tomograms with a known spacing therebetween, and generating several profiles therefrom. Then, the respective profiles are aligned in a CAD program with the known spacing in an anatomically correct way. Thereafter, the three-dimensional solid model of the jawbone is generated by expanding or lofting the respective profiles, with the resulting solid model being spanned over each profile.

Apart from that, it is possible, although more cumbersome, to generate two separate FE models of the jawbone and the implant at first and then to combine them in the FE program.

The model of the jawbone may also be combined with models other than the implant model such as with a model of a tooth. Furthermore, it is possible to extend the model of the jawbone combined with the implant beyond the area of the gash, so that the teeth adjacent to the gash are included.

The overall process can be simplified by using a device which is specifically adapted to the application, in which the image processing steps of the data processor are adjusted to the tomograms taken by the equipment and in which the data processing steps of the CAD program are linked and automated to the greatest possible extent. In such a device it is not necessary that the equipment and the data processor are directly coupled with each other, nor it is necessary that the data processing steps are executed in one and the same data processor. Instead of a closed system, it is also possible that the treating dentist sends the tomogram(s) of the patient or the finished jaw model to the manufacturer of the implants who selects or produces a compatible implant on this basis accurate to size. If, on the other hand, the implant selection is on the side of the treating dentist, the dentist could be supplied by manufacturers with design data or models of the available implants.

The above-mentioned FE models of the jawbone combined with the implant and/or tooth may not only be used for calculating the distribution of stress or strain and deformation, but also for calculating distributions of temperature in case there is a temperature difference across the implant, or for a frequency analysis in case of an ultrasonic calculus treatment on the implant or tooth.

The method, the device and the computer software for generating the jaw model are useful not only in the development of dental implants or pre-operative planning of implants, but the solid models and FE models of the jawbone generated as discussed above may also be used in principle for illustrating and simulating oral surgery, for adjusting dentures seated on the jawbone, or for planning corrections of defective dental positions. A further application is generating models of a fractured jawbone by combining the three-dimensional model of the jawbone with three-dimensional models of metal plates and screws used for stabilizing the fracture.

The invention claimed is:

1. A method for generating an individual model of a jawbone segment spanning a procedure site, the procedure site being an area of the jawbone subject to a prospective dental or surgical procedure, the method steps comprising:
    obtaining a single digital tomogram of the jawbone near the procedure site, wherein the tomogram is formed approximately perpendicular to the longitudinal axis of the jawbone segment in the area spanning the procedure site;
    determining the outer boundary between the compact portion of the jawbone and the surrounding tissue based on the tomogram;
    creating a two-dimensional profile of the cross section of the jawbone based on the outer boundary; and
    extruding the profile along its approximate planar normal vector in the direction of the procedure site to obtain an approximated three-dimensional solid model of the jawbone segment spanning the procedure site.

2. The method of claim 1, the method steps further comprising:

determining the inner boundary between the compact portion of the jawbone and the spongiosal portion of the jawbone based on the tomogram, wherein the two-dimensional profile of the cross section of the jawbone is further based on the inner boundary, and wherein the approximated three-dimensional solid model comprises both the spongiosal and compact jawbone segments.

3. The method of claim 2, the method steps farther comprising:

generating a three-dimensional finite element model from the solid model of the spongiosal and compact jawbone segment.

4. The method of claim 1, the method steps further comprising:

combining the solid model of the jawbone segment with a solid model of a dental implant or tooth to obtain a combined three-dimensional solid model of the jawbone segment and the dental implant or tooth.

5. The method of claim 4, the method steps further comprising:

generating a three-dimensional finite element model from the combined solid model of the jawbone segment and the dental implant or tooth.

6. The method of claim 5, wherein different material properties are assigned to the jawbone segment and/or the dental implant or tooth when generating the finite element model.

7. The method of claim 6, the method steps further comprising:

calculating, by means of the finite element model, the distribution of stress in the jawbone when a force acts on the dental implant or tooth.

8. A system for generating an individual model of a jawbone segment spanning a procedure site, the procedure site being an area of the jawbone subject to a prospective dental or surgical procedure, the system comprising:

an imaging apparatus for generating a single tomogram of the jawbone near the procedure site, wherein the tomogram is formed approximately perpendicular to the longitudinal axis of the jawbone segment in the area spanning the procedure site; and a computing means for performing the processing steps comprising:
digitizing the tomogram if the tomogram is analog;
determining the outer boundary between the compact portion of the jawbone and the surrounding tissue based on the tomogram;
creating a two-dimensional profile of the cross section of the jawbone based on the outer boundary; and
extruding the profile along its approximate planar normal vector in the direction of the procedure site to obtain an approximated three-dimensional solid model of the jawbone segment spanning the procedure site.

9. The system of claim 8, wherein the processing steps further comprising:

determining the inner boundary between the compact portion of the jawbone and the spongiosal portion of the jawbone based on the tomogram, wherein the two-dimensional profile of the cross section of the jawbone is further based on the inner boundary, and wherein the approximated three-dimensional solid model comprises both the spongiosal and compact jawbone segments.

10. The system of claim 9, wherein the processing steps further comprising:

generating a three-dimensional finite element model from the solid model of the spongiosal and compact jawbone segment.

11. The system of claim 8, wherein the processing steps further comprising:

combining the solid model of the jawbone segment with a solid model of a dental implant or tooth to obtain a combined three-dimensional solid model of the jawbone segment and the dental implant or tooth.

12. The system of claim 11, wherein the processing steps further comprising:

generating a three-dimensional finite element model from the combined solid model of the jawbone segment and the dental implant or tooth.

13. The system of claim 12, wherein different material properties are assigned to the jawbone segment and/or the dental implant or tooth when generating the finite element model.

14. The system of claim 13, wherein the processing steps further comprising:

calculating, by means of the finite element model, the distribution of stress in the jawbone when a force acts on the dental implant or tooth.

15. A computer program product comprising a computer-readable medium having instructions, the instructions when executed by a processor cause a computer to execute a process for generating an individual model of a jawbone segment spanning a procedure site, the procedure site being an area of the jawbone subject to a prospective dental or surgical procedure, the process comprising:

digitizing the tomogram if the tomogram is analog;
determining the outer boundary between the compact portion of the jawbone and the surrounding tissue based on the tomogram;
creating a two-dimensional profile of the cross section of the jawbone based on the outer boundary; and
extruding the profile along its approximate planar normal vector in the direction of the procedure site to obtain an approximated three-dimensional solid model of the jawbone segment spanning the procedure site.

16. The computer program product of claim 15, the program instructions further comprising:

determining the inner boundary between the compact portion of the jawbone and the spongiosal portion of the jawbone based on the tomogram, wherein the two-dimensional profile of the cross section of the jawbone is further based on the inner boundary, and wherein the approximated three-dimensional solid model comprises both the spongiosal and compact jawbone segments.

17. The computer program product of claim 16, the program instructions further comprising:

generating a three-dimensional finite element model from the solid model of the spongiosal and compact jawbone segment.

18. The computer program product of claim 15, the program instructions further comprising:

combining the solid model of the jawbone segment with a solid model of a dental implant or tooth to obtain a combined three-dimensional solid model of the jawbone segment and the dental implant or tooth.

19. The computer program product of claim 18, the program instructions further comprising:

generating a three-dimensional finite element model from the combined solid model of the jawbone segment and the dental implant or tooth.

20. The computer program product of claim 19 wherein different material properties are assigned to the jawbone segment and/or the dental implant or tooth when generating the finite element model.

21. The computer program product of claim 20, the program instructions further comprising:
calculating, by means of the finite element model, the distribution of stress in the jawbone when a force acts on the dental implant or tooth.

* * * * *

UNITED STATES PATENT AND TRADEMARK OFFICE
CERTIFICATE OF CORRECTION

PATENT NO. : 7,383,163 B2 Page 1 of 1
APPLICATION NO. : 10/502555
DATED : June 3, 2008
INVENTOR(S) : Christof Holberg It is certified that error appears in the above-identified patent and that said Letters Patent is hereby corrected as shown below:

On the title page, item [54] and column 1, lines 2-3.

In the Title:
Please delete "PRODUCT" and insert --SOFTWARE-- therefore.
Please remove the dash "-" from "JAW-BONE" to read correctly as --JAWBONE--.

Column 7:
Claim 3, line 1, please delete "farther" and insert --further-- therefore.

Signed and Sealed this

Twenty-sixth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,383,163 B2 | Page 1 of 1 |
| APPLICATION NO. | : 10/502555 | |
| DATED | : June 3, 2008 | |
| INVENTOR(S) | : Christof Holberg | |

It is certified that error appears in the above-identified patent and that said Letters Patent is hereby corrected as shown below:

On the title page, item [54] and column 1, lines 2-3.

In the Title:
Please delete "PRODUCT" and insert --SOFTWARE-- therefore.
Please remove the dash "-" from "JAW-BONE" to read correctly as --JAWBONE--.

Column 7:
Claim 3, line 10, please delete "farther" and insert --further-- therefore.

This certificate supersedes the Certificate of Correction issued August 26, 2008.

Signed and Sealed this

Twenty-third Day of September, 2008

JON W. DUDAS
*Director of the United States Patent and Trademark Office*